(12) United States Patent
Watschke et al.

(10) Patent No.: US 7,303,525 B2
(45) Date of Patent: Dec. 4, 2007

(54) SURGICAL ARTICLE AND METHODS FOR TREATING FEMALE URINARY INCONTINENCE

(75) Inventors: Brian P. Watschke, Eden Prairie, MN (US); Robert E. Lund, St. Michael, MN (US); Kimberly A. Anderson, Eagan, MN (US)

(73) Assignee: AMS Research Corporation, Minnetonka, MN (US)

( * ) Notice: Subject to any disclaimer, the term of this patent is extended or adjusted under 35 U.S.C. 154(b) by 622 days.

(21) Appl. No.: 10/645,588

(22) Filed: Aug. 22, 2003

(65) Prior Publication Data

US 2005/0043580 A1 Feb. 24, 2005

(51) Int. Cl.
*A61F 2/02* (2006.01)
(52) U.S. Cl. .......................................... 600/30
(58) Field of Classification Search ............ 600/29–31; 606/151–156
See application file for complete search history.

(56) References Cited

U.S. PATENT DOCUMENTS

| | | | |
|---|---|---|---|
| 5,112,344 A | 5/1992 | Petros et al. | 606/148 |
| 5,611,515 A | 3/1997 | Benderev et al. | 128/898 |
| 5,774,854 A | 6/1998 | Sharman | |
| 5,842,478 A | 12/1998 | Benderev et al. | 128/898 |
| 5,860,425 A | 1/1999 | Benderev et al. | 128/898 |
| 5,899,909 A | 5/1999 | Claren et al. | 606/119 |
| 6,039,686 A | 3/2000 | Kovac | 600/30 |
| 6,042,534 A | 3/2000 | Gellman et al. | 600/30 |
| 6,110,101 A | 8/2000 | Tihon et al. | 600/37 |
| 6,385,586 B1 | 5/2002 | Dietz | |
| 2001/0018549 A1* | 8/2001 | Scetbon | 600/30 |
| 2002/0156487 A1 | 10/2002 | Gellman | 606/139 |
| 2002/0156488 A1* | 10/2002 | Gellman et al. | 606/139 |
| 2004/0039246 A1* | 2/2004 | Gellman et al. | 600/30 |
| 2004/0116944 A1* | 6/2004 | Chu et al. | 606/151 |

FOREIGN PATENT DOCUMENTS

WO WO 2004/016180 A2 2/2004

OTHER PUBLICATIONS

U.S. Appl. No. 10/645,588, filed Aug. 22, 2003, Watschke et al.
U.S. Appl. No. 10/793,903, filed Mar. 8, 2004, Lund et al.

(Continued)

*Primary Examiner*—Ahmed Farah
*Assistant Examiner*—Christine D. Hopkins
(74) *Attorney, Agent, or Firm*—Jose W. Jimenez; Kimberly K. Baxter

(57) ABSTRACT

A sling assembly including a surgical sling configured to be implanted during a surgical sling procedure. The sling includes first and second regions and a central portion. The sling assembly further includes a removable sheath assembly situated about the surgical sling. The removable sheath assembly includes first and second upper sheaths. The first upper sheath is configured to be situated about the first region of the surgical sling, and the second upper sheath is configured to be situated about the second region of the surgical sling. The removable sheath assembly further includes a lower sheath. The lower sheath is configured to be situated about the central portion of the surgical sling and to be in cooperative association with both the first and second upper sheaths.

15 Claims, 13 Drawing Sheets

OTHER PUBLICATIONS

Atherton M.J., et al., "A Comparison of Bladder Neck Movement and Elevation After Tension-free Vaginal Tape and Colposuspension", *British Journal of Obstetrics and Gynecology*, Nov. 2000, vol. 17, p. 1366-1370.

Nilsson et al., "The Tension-free Vaginal Tape Procedure is Successful in the Majority of Women with Indications for Surgical Treatment of Urinary Stress Incontinence", *British Journal of Obstetrics and Gynecology*, Apr. 2001, vol. 108, p. 414-419.

Ullmsten et al., An Ambulatory Surgical Procedure Under Local Anesthesia for Treatment of Female Urinary Incontinence, *Int. Urogynecol. J.* (1996), v. 7, pp. 81-86.

* cited by examiner

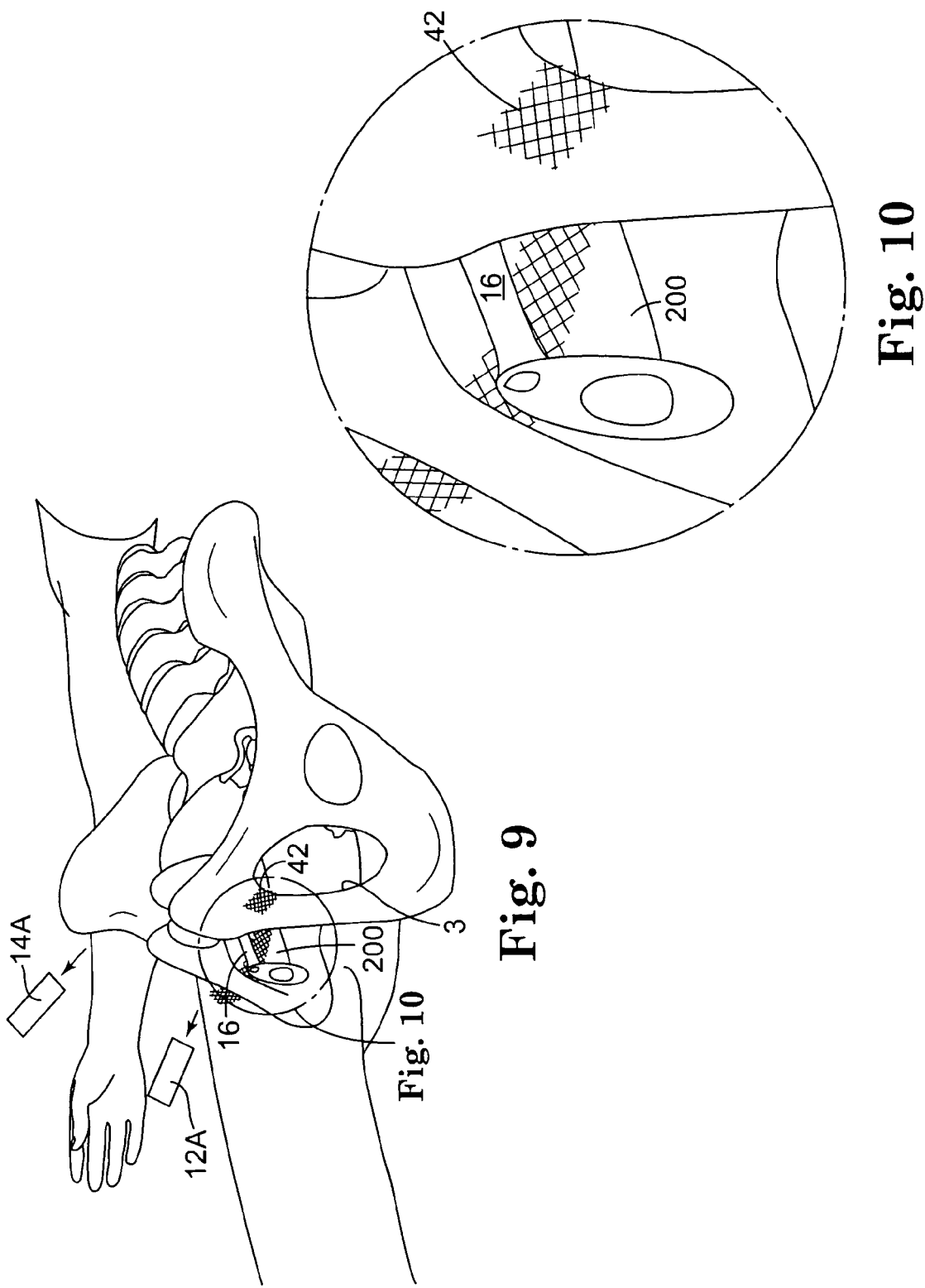

SURGICAL ARTICLE AND METHODS FOR TREATING FEMALE URINARY INCONTINENCE

BACKGROUND OF THE INVENTION

1. Field of the Invention

The present invention relates generally to a surgical instrument and a method for treating female urinary incontinence.

2. Description of the Related Art

Urinary incontinence is a significant health concern worldwide. Incontinence may occur when the pelvic floor weakens. There are five basic types of incontinence: stress incontinence, urge incontinence, mixed incontinence, overflow incontinence and functional incontinence. There are a large number of surgical interventions and procedures for addressing incontinence.

A variety of surgical procedure options are currently available to treat incontinence. Depending on age, medical condition, and personal preference, surgical procedures can be used to completely restore continence. One type of procedure, found to be an especially successful treatment option for Stress Urinary Incontinence in both men and women, is a sling procedure.

A sling procedure is a surgical method involving the placement of a sling to stabilize or support the bladder neck or urethra. There are a variety of different sling procedures. Descriptions of different sling procedures are disclosed in U.S. Pat. Nos. 5,112,344; 5,611,515; 5,842,478; 5,860,425; 5,899,909; 6,039,686, 6,042,534 and 6,110,101.

Sling procedures differ in the type of material used for the sling, the method of anchoring the sling material in the body and how the sling material is inserted in the body. The time required for a surgical procedure varies, but is preferably as short as possible. This factor is frequently reported in urology and gynecology literature. See Atherton M. J., et al., A Comparison of Bladder Neck Movement and Elevation After Tension-free Vaginal Tape and Colposuspension, British Journal of Obstetrics and Gynecology, November 2000, Vol. 17, p. 366-1370, Nilsson et al, The Tension-free Vaginal Tape Procedure is Successful in the Majority of Women with Indications for Surgical Treatment of Urinary Stress Incontinence, British Journal of Obstetrics and Gynecology, April 2001, Vol. 108, P. 414-419; and Ulmsten et al., An Ambulatory Surgical Procedure Under Local Anesthesia For Treatment of Female Urinary Incontinence, Int. Urogynecol. J. (1996), v. 7, pps. 81-86.

Although serious complications associated with sling procedures are infrequent, they do occur. Complications include urethral obstruction, development of de novo urge incontinence, hemorrhage, prolonged urinary retention, infection, and damage to surrounding tissue and sling erosion. Infection may occur as a result of exposing contaminants from the vagina during the removal of prior art two piece overlapping sheath assemblies via either suprapubic incisions or groin incisions. A two piece overlapping sheath assembly is disclosed in published U.S. patent application No. 2002/0156487-A1.

Many slings include a protective sheath used during insertion of the sling. After the sling is implanted, the sheath is removed and discarded. The protective sheath is generally constructed of a material that affords visual examination of the implantable sling and that affords smooth passage of the sling assembly through tissue of the patient.

In many cases, the sheath is made of polyethylene. Other materials used to construct the sheath include polypropylene, nylon, polyester or Teflon. The sheath material should be flexible and provide sufficient structural integrity to withstand the various forces exerted on the sheath throughout the sling delivery procedure. Referring to FIG. 14, the sheath 44 is configured to have sufficient flexibility to facilitate user manipulation and adequate structural strength to withstand the various forces applied to the sheath 44 during delivery and/or positioning of the sling assembly. It should also conveniently separate from the sling material after the sling is implanted without materially changing the position of the sling.

The sheath 44 may comprise two elongate, separable sections 86. Portion S of the sheath 44 detachably and telescopically overlap near the middle portion of the sling. During sheath removal, the first section and the second section of the sheath are slid off the sling by pulling each end 86 of the sheath 44 away from the middle portion of the sling assembly. Removal of the sheath 44 causes separation of the overlapping sheath sections, thereby exposing the sling.

The problem with the telescoping configuration of the first and second sections of the sheath 44 is that there has been a tendency for the two telescoping sections to "stick" to one another during the removal process believed to be due to either friction caused by the respective telescoping sections of the sheath or use of a spacer such as a clamp under the urethra. In the latter, the spacer increases the friction between the two sheaths and causes them to stick. That is, the overlapping section of the first and second sections of the sheath is situated at the point of maximum curvature and hence the point of maximum interference/friction.

SUMMARY OF THE INVENTION

Accordingly, it is an object of the present invention to provide a sling assembly including a sheath assembly that is easily removed from a surgical sling after the sling assembly is situated under the patient's urethra, the sheath assembly including two upper sheaths and a lower sheath.

Further, it is an object of the present invention to provide a spacer configured to be placed between the surgical sling and the patient's urethra after the portion of the sheath assembly situated below the patient's urethra (i.e., the lower sheath) has been removed.

Further, it is an object of the present invention to reduce the amount of exposed material moved from the vaginal region to another part of the patient's body (e.g., the abdominal or groin region);

Finally, it is an object of the present invention to provide a method for removing the three piece sheath assembly after the sling assembly has been placed under the urethra.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 9 illustrates the process of removing the two upper sheaths after the surgical sling has been positioned underneath the patient's urethra using the trans-obturator sling assembly system;

FIG. 10 is a magnified view of the pubic area illustrated in FIG. 9;

DETAILED DESCRIPTION OF THE PREFERRED EMBODIMENTS

Figure 1:
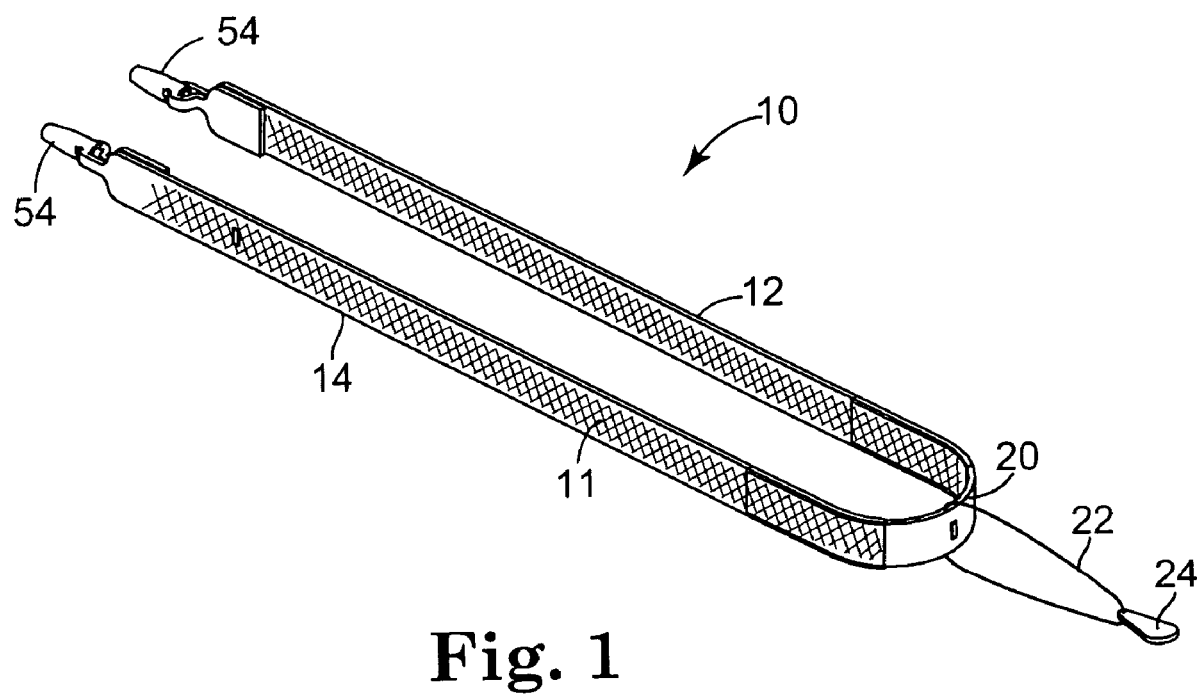
FIG. 1 is a perspective view of a sling assembly having a three piece removable sheath according to the present invention.

Referring now to the drawings, wherein like reference numerals designate identical or corresponding parts throughout the several views. FIG. 1 illustrates a sling assembly 10 including a surgical sling 11 and three sheaths, two upper sheaths 12 and 14 and a lower sheath 20. The sling 11 and the three sheaths 12, 14, and 20 are made of biocompatible materials having sufficient strength and structural integrity to withstand the various forces exerted upon these components during an implant procedure and/or following implantation within a patient. Suitable implantable materials (i.e., slings) associated with the present invention include synthetic and non-synthetic materials. Suitable non-synthetic implantable materials include human fascia lata, treated animal (e.g. bovine or porcine or equine pericardium) tissue, autologous tissue, cadaver tissue, homografts, xenografts, heterografts, allografts and combinations of such materials. Suitable synthetic materials include knitted polypropylene slings alone, such slings with surrounding sheaths, or silicone coated polymer slings, such as those described in published U.S. patent application No. 2002/0072694-A1.

The sheaths 12, 14, and 20 are preferably made of polyethylene. Other materials including, without limitation, polypropylene, nylon, polyester, or Teflon can also be used. In a preferred embodiment, the sling comprises a mesh material. The mesh material may comprise one or more woven, knitted or inter-linked filaments or fibers that form multiple fiber junctions throughout the mesh. The filaments may comprise monofilaments or braided filament. The fiber junctions may be formed via weaving, knitting, braiding, bonding, ultrasonic welding or other junction forming techniques, including combinations thereof. In addition, the size of the resultant openings or pores of the mesh may be sufficient to allow tissue in-growth and fixation within surrounding tissue. As an example, not intended to be limiting, the holes may comprise polygonal shaped holes with diagonals of 0.132 inches and 0.076 inches.

The quantity and type of fiber junctions, fiber weave, pattern, and material type influence various sling properties or characteristics. As another example, not intended to be limiting, the mesh may be woven polypropylene monofilament, knitted with a warp tricot. The stitch count may be 27.5 courses/inch (+ or − 2 courses ) and 13 wales/inch (+ or − 2 wales). The thickness of this example is 0.024 inches. Non-mesh sling configurations are also included within the scope of the invention. In a one embodiment, a polypropylene sling mesh is constructed of polypropylene monofilament. The mesh may be precut to a predetermined size (e.g. about 1.1 cm width×35 cm length). An absorbable tensioning suture is preferably threaded into the length of the sling mesh to allow for tensioning adjustment of the sling mesh after placement in the patient is achieved.

In a preferred embodiment, the mesh is preferably an elastic, as opposed to a substantially inelastic mesh. A test for differentiating between elastic meshes and substantially inelastic meshes is disclosed in U.S. Pat. application Ser. No. 10/386,897, filed Mar. 11, 2003 (the entire contents of which are herein incorporated by reference).

Dilators 54 are optionally attached to the ends of the sling assembly 10. The dilators 54 atraumatically create and/or expand the passageway through the tissues for sling assembly delivery.

Figure 11:
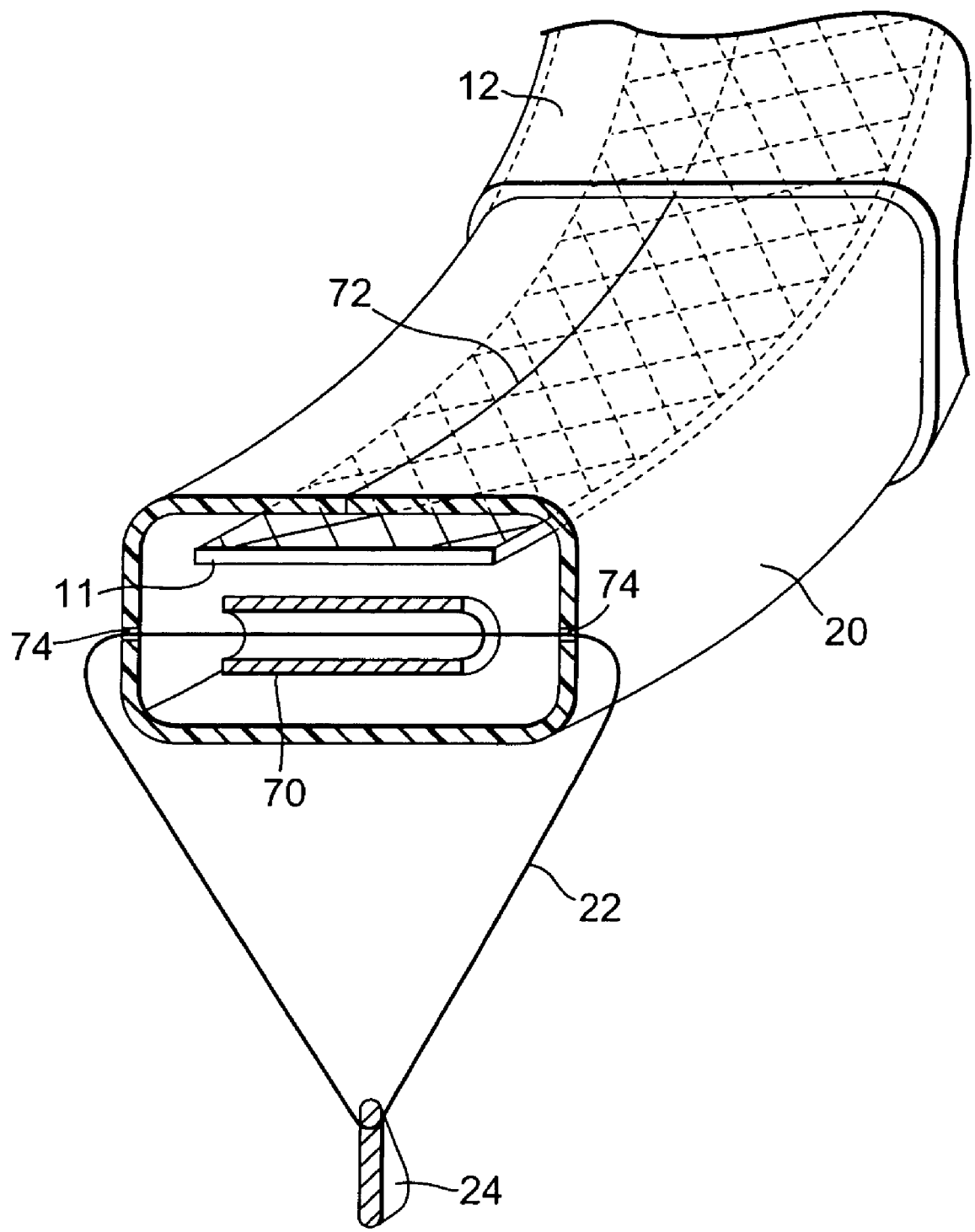
FIG. 11 is a cross-sectional view of the lower sheath and the surgical sling.

Tab portion 24 is preferably connected to the lower sheath 20 via suture 22. Tab portion 24 is designed and shaped to be pulled by the thumb and one of the fingers through a vaginal incision of the patient. A cross-sectional view is shown in FIG. 11. As can be seen from FIG. 11, a removal assembly including a tube 70 is situated within lower sheath 20 below sling 11. The longitudinal length of the tube 70 is perpendicular to the longitudinal length of the lower sheath 20. Further, the tube 70 is preferably situated at the midportion of the lower sheath 20 measured lengthwise. Through holes 74 are placed in the lower sheath 20 adjacent the ends of the tube 70. Suture 22 is a closed loop threaded through holes 74 and a hole placed in tab 24. Alternatively, the suture 22 is fastened to tab 24 using any biocompatible adhesive. In either case, the removal assembly should have sufficient strength and structural integrity to withstand the force necessary to remove the lower sheath 20 from the sling 11 by pulling on the tab 24.

FIG. 11 further illustrates the relationship between upper sheath 12 and lower sheath 20. The lower sheath 20 can be placed telescopically within upper sheath 12 as illustrated in FIG. 11. Alternatively, the upper sheaths 12 and 14 can be placed telescopically within the lower sheath 20. A slit 72 is placed along the longitudinal length of the lower sheath 20 in order to allow the lower sheath 20 to be removed from the sling 11 when the tab 24 is pulled. Alternatively, the slit can comprise a score or other weakening of the sheath material including a kiss cut.

Figure 2:
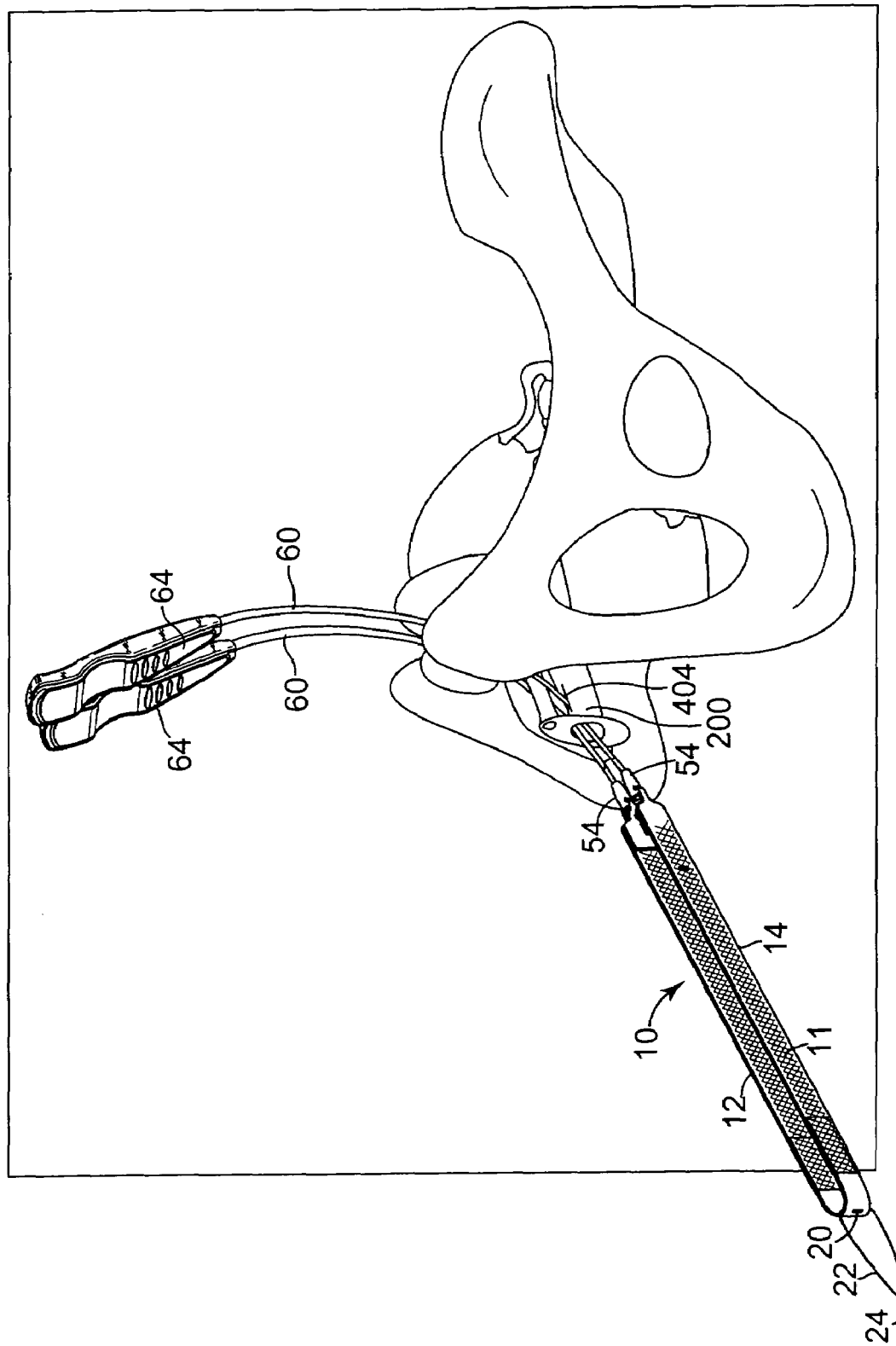
FIG. 2 is a perspective view of the pubic area of a patient relative to a sling assembly including two needles, two dilators, a surgical sling, and a three piece sheath assembly according to the present invention prior to the surgical sling and the sheath assembly being placed under the patient's urethra using a suprapubic approach.

FIG. 2 illustrates the sling assembly 10 of the present invention in conjunction with needles 60 and handles 64 used in a suprapubic approach. The sling assembly 10 may be implanted by a wide variety of surgical approaches such as transabdominal (i.e. suprapubic or from above), transvaginal (from below), or transobturator (e.g. with the sling anchored in the obturator foramen). Various surgical tools for implanting sling assemblies, sling assemblies and surgical approaches are disclosed in U.S. Pat. No. 6,612,977; published U.S. patent application Nos. 2002-0107430-A1, 2002-0147382, 2002-0099258-A1 and US-2002-0099259-A1; and U.S. pat. application Ser. No. 10/306,179 filed Nov. 27, 2002, all of the above incorporated herein by reference thereto. The dilators 54 dilate a needle track for ease of sling introduction and positioning within the patient. An end of the needle 60 is preferably keyed to allow for convenient, secure attachment of the needle 60 relative to the dilator 54.

Figure 3:
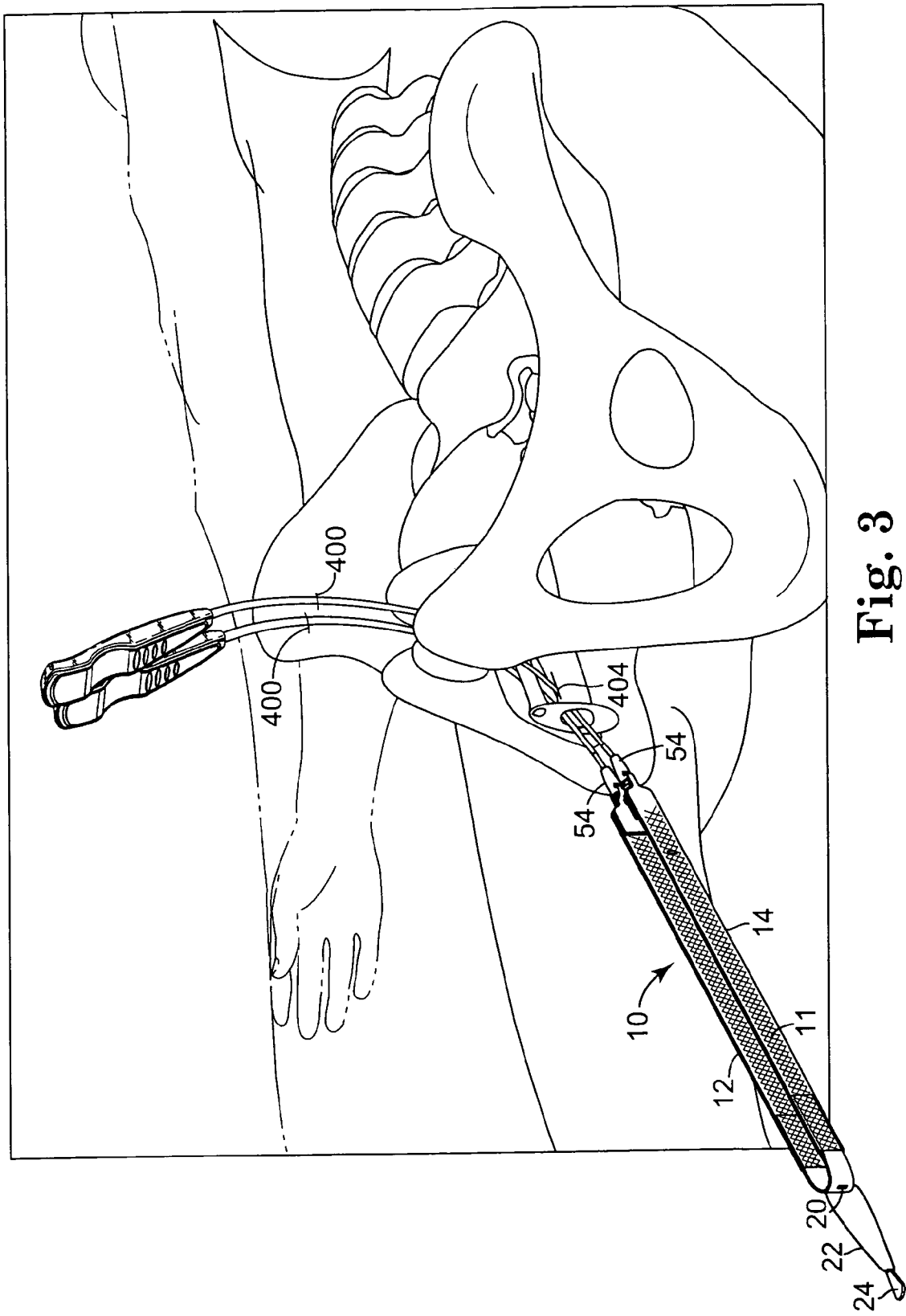
FIG. 3 illustrates the two needles as they are withdrawn through two suprapubic incisions in order to position the surgical sling and the protective sheath under the patient's urethra.

The dilator 54 atraumatically creates and/or expands the passageway through the tissues for sling assembly delivery. The dilator 54 is short relative to a needle 60 for ease of passage of the assembly and to reduce the overall amount of tissue that is deflected at one time. The dilator is less than 2.5 inches in length. The maximum radius of a dilator 54 is less than 10 mm. The tip of the dilator 54 is blunt, as the leading tip of the dilator 54 will pass through tissue that has already been pierced by a needle 60. As shown in FIG. 2, the needles 60 have been passed downward through a vaginal incision 404 and out the vagina 200. The sling assembly has been associated with the needles 60 using dilators 54. FIG. 3 further illustrates suprapubic incisions 400. The suprapubic incisions 400 enable the needles to be passed downward through the vaginal incision 404.

Figure 4:
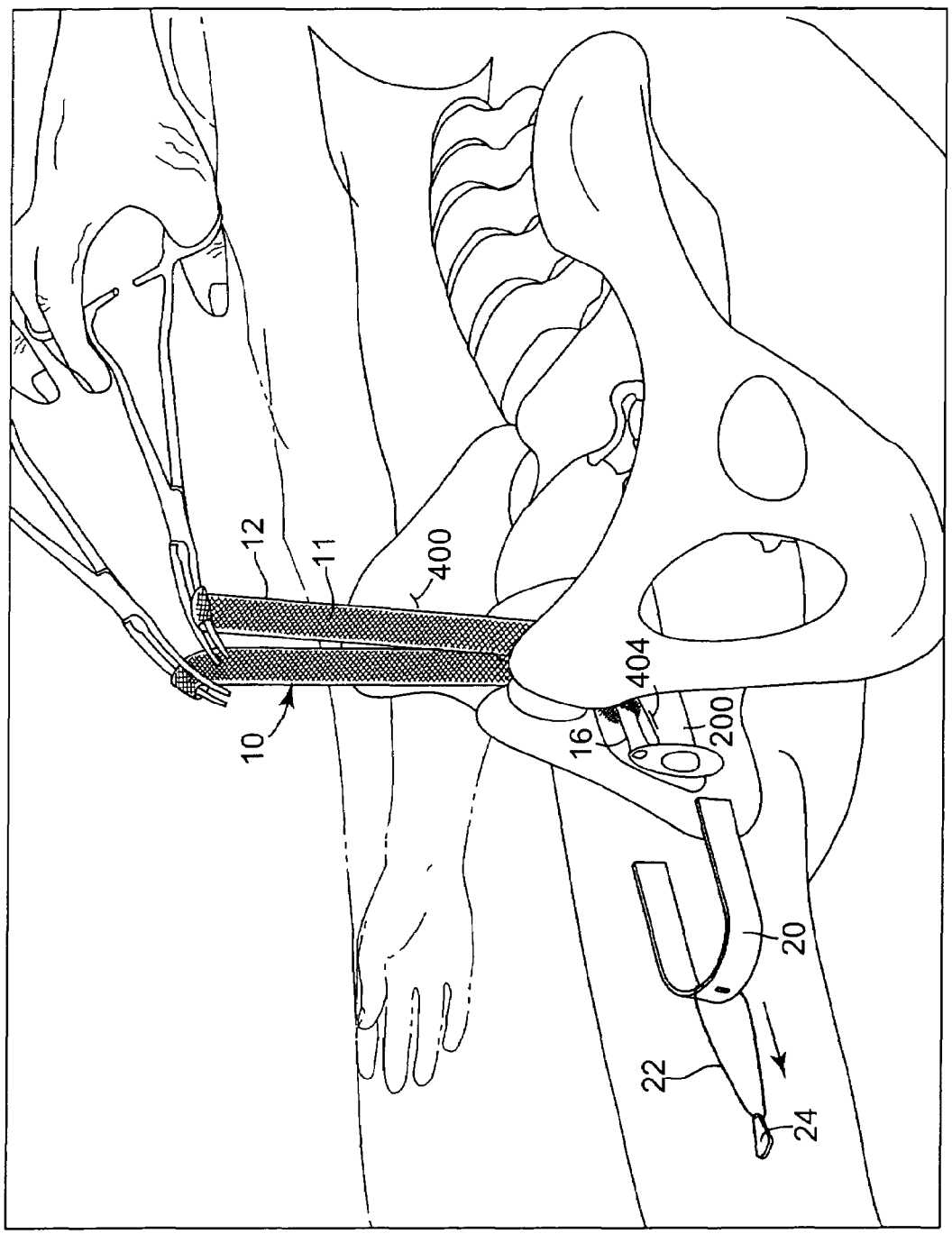
FIG. 4 illustrates a process of removing the lower sheath after the surgical sling has been positioned underneath the patient's urethra.

FIG. 4 illustrates the positioning of the sling assembly 10 underneath the urethra 16. The lower sheath 20 has been removed by pulling the tab 24 through the vaginal incision 404 and the vagina 200. Thus, exposing the sling 11. Because the lower sheath 20 is situated adjacent the urethra 16, the lower sheath 20 is the sheath most exposed to vaginal contaminants of the three sheaths including upper sheaths 12 and 14. The position where lower sheath 20 is placed relative to the urethra 16 substantially corresponds to the position of the overlapping portion S of the prior art sheath relative to the urethra. Both the lower sheath 20 and the overlapping portion of the prior art sheath are the most exposed portions of their respective sling assemblies. That is, those portions are exposed to the contaminants of the vaginal region. However, because in the present invention, the lower sling 20 is removed through vaginal incision 404 as opposed to a suprapubic incision, the lower sling 20 is not exposed to the body during removal thereof. FIG. 4 further shows the sling after the dilators 54 have been cut off, but prior to final trimming.

Figure 12:
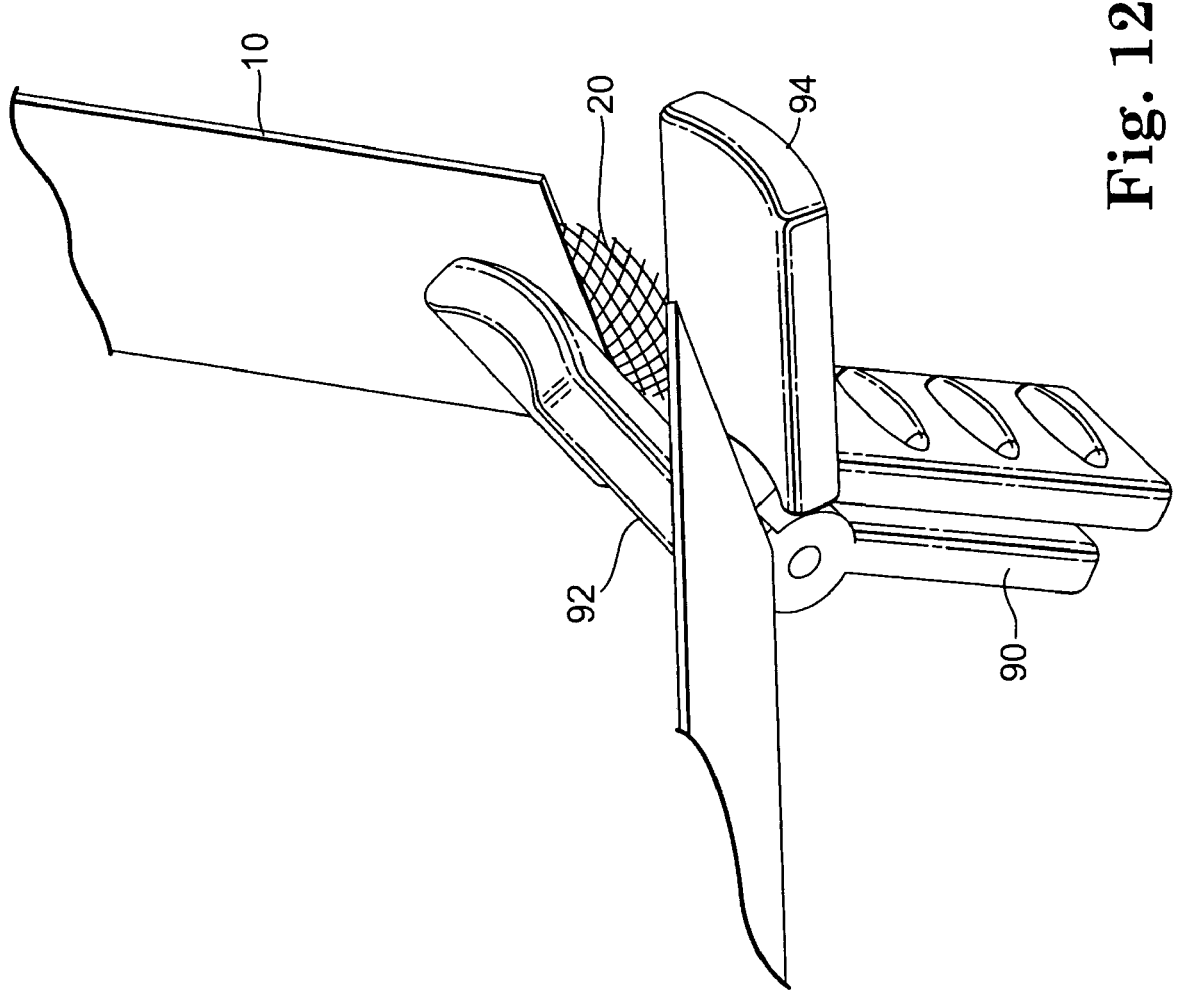
FIG. 12 is a perspective view of a spacer mechanism with jaws open.
Figure 13:
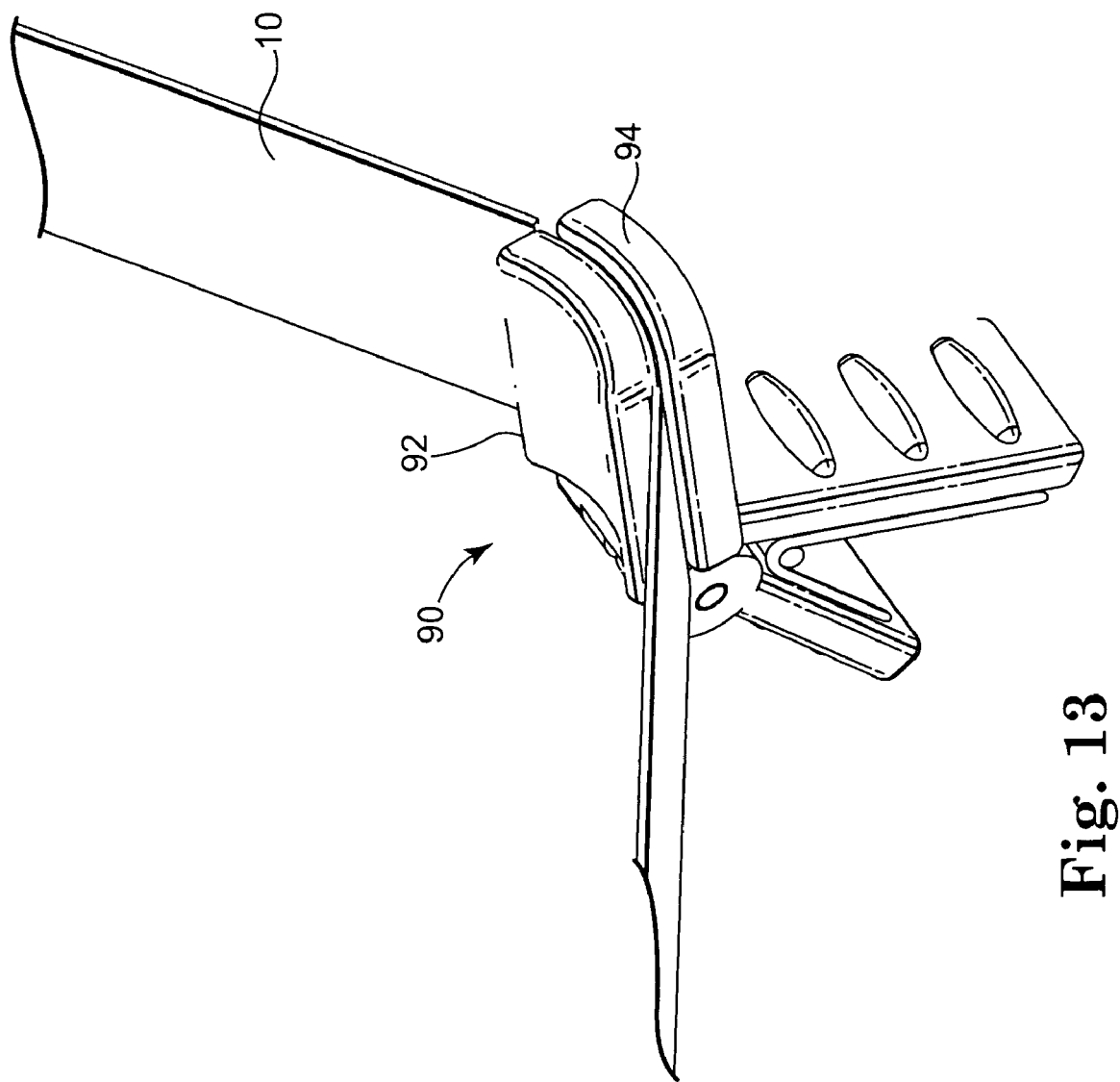
FIG. 13 is a perspective view of a spacer mechanism with jaws closed.
Figure 14:
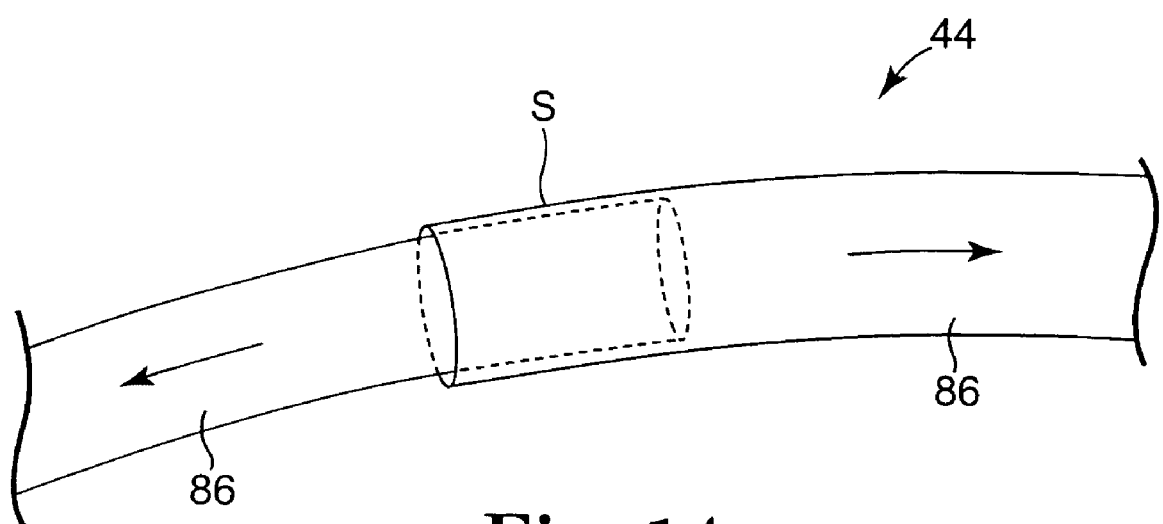
FIG. 14 is a perspective view of the prior art sheath assembly.

In another embodiment, a spacer is inserted between the exposed sling and the patient's urethra until final positioning and tensioning adjustments are made to the sling 11. The spacer can be for example a Hegar dilator, scissors, or Metzenbaum clamps, etc. Alternatively, the spacer can be a device as shown in FIGS. 12 and 13. See also U.S. patent application Ser. No. 10/646,082 entitled Surgical Article and filed on Aug. 22, 2003. FIGS. 12 and 13 illustrate a spacer 90 including jaws 92 and 94. FIG. 12 illustrates the jaws 92 and 94 in an open state. The jaws 92 and 94 are positioned over and below the sling assembly 10 in a position where the jaws would clamp the lower sheath 20 when closed. FIG. 13 illustrates the jaws 92 and 94 clamped on the sheath assembly 10. Since the lower sheath 20 and the upper sheaths 10 and 12 do not overlap in the center of the sling underneath the urethra 16 and the assembly 10 is not tensioned against a spacer, the lower sheath 20 is easily removed. The upper sheaths 12 and 14 remain associated with the sling 11 at this time. According to one embodiment, a spacer (e.g., spacer 90) remains between the exposed sling and the urethra while the upper sheaths 12 and 14 are removed. Because the upper sheaths 12 and 14 do not overlap the lower sheath 20 at the center of the sling 11 underneath the urethra and the sling assembly 10 is not tensioned against a spacer, the upper sheaths 12 and 14 can be removed easily.

In another embodiment, the upper sheaths 12 and 14 are removed prior to removing the lower sheath 20 (no spacer is used). Because sheaths are designed to aid in passing the sling into the body with little resistance, if the upper sheaths are not removed prior to removing the lower sheath, the sling may slide up when the upper sheaths are pulled and could cause over tensioning of the sling, placing the patient in retention. By removing the upper sheaths first, the sling is exposed to the patient's tissue anchoring the sling in place for the removal of the lower sheath.

According to another embodiment, a time advantage may be obtained by using a spacing mechanism (e.g., spacer 90) and by removing the upper sheaths first. This is due to the fact that if the upper sheaths 12 and 14 are removed prior to removing the lower sheath, the sling will become anchored into the body. If this is done with a spacing mechanism in place, the sling is anchored at the right tension. The spacing mechanism can then be removed and the lower sheath 20 removed vaginally without affecting the tension. By allowing the spacer mechanism to be placed over the lower sheath 20, the surgical method does not require the step of attaching the spacing mechanism to the sling after insertion of the sling and removal of the lower sheath 20. According to another embodiment, the sling assembly could be provided with the spacer integrated thereto. Another advantage would be that the sling can be pulled to the proper tension when removing the needles and the attached sling assembly rather than having to leave the sling initially loose to allow placement of the spacer between the urethra and sling after removing the lower sheath.

Figure 5:
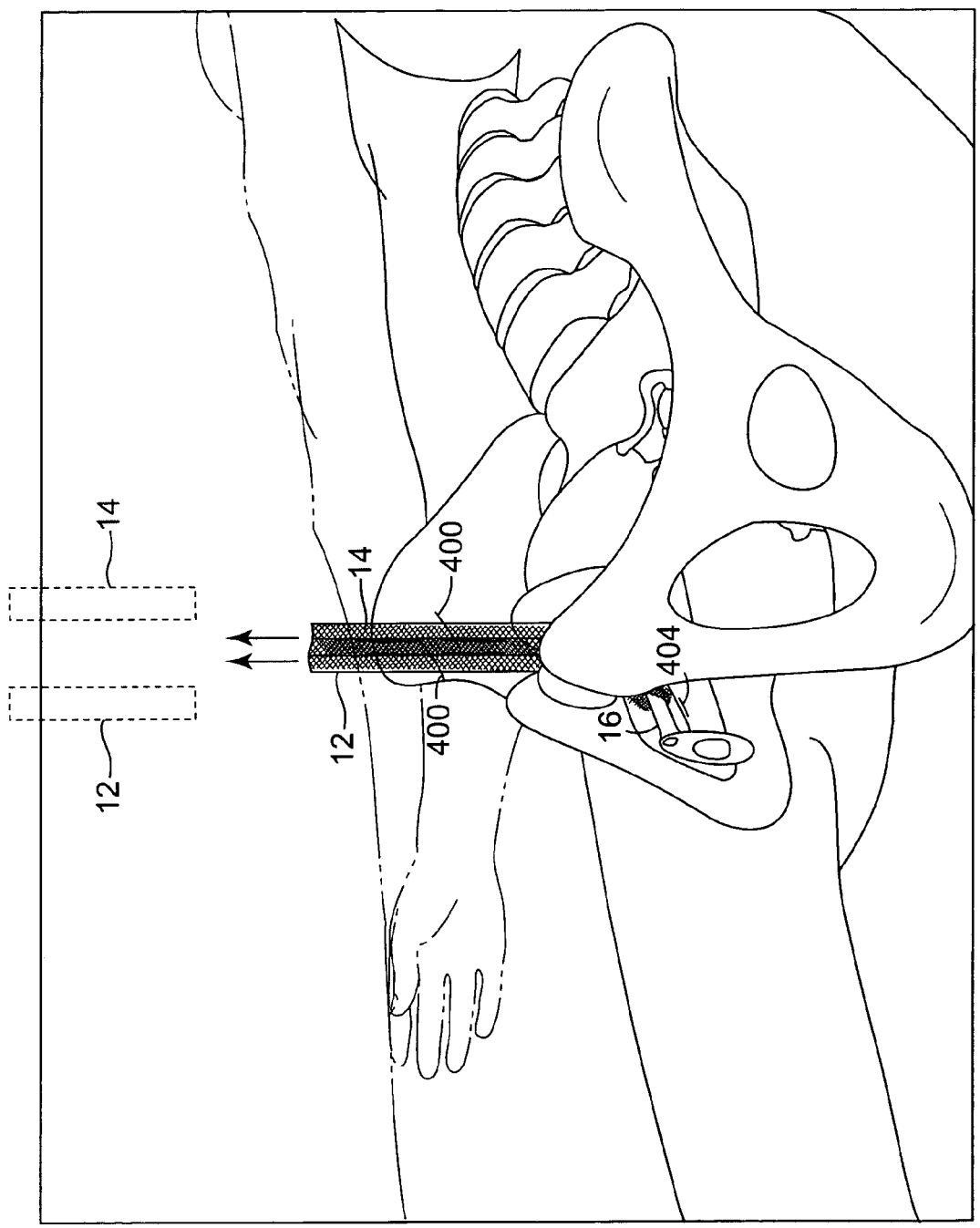
FIG. 5 illustrates the process of removing the two upper sheaths after the lower sheath has been removed.
Figure 6:
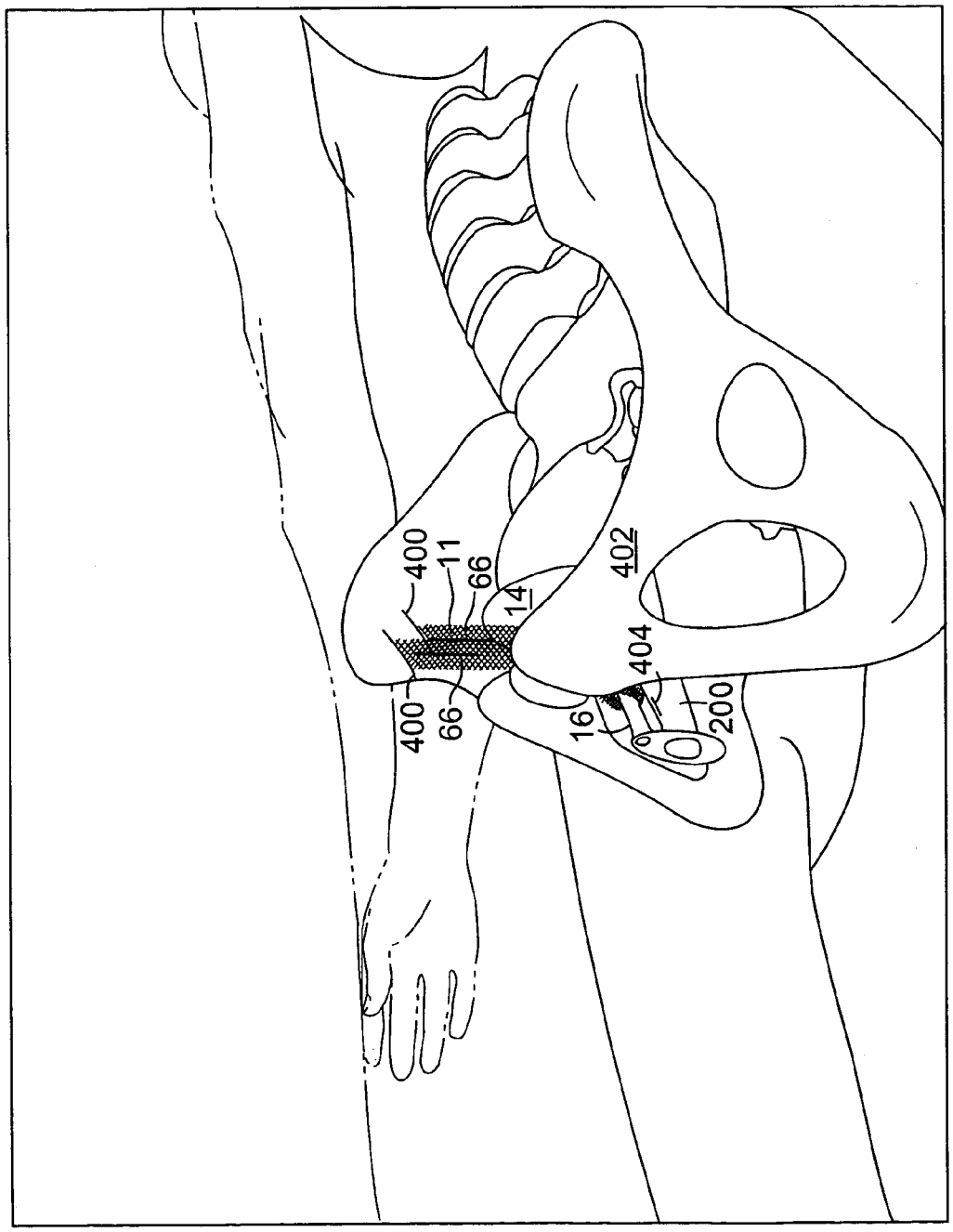
FIG. 6 illustrates the placement of the surgical sling after the sheath assembly has been removed and the ends of the sling assembly have been cut-off at the suprapubic incisions.

FIG. 5 illustrates removing the upper sheaths 12 and 14 through the suprapubic incisions 400. The final placement of the sling assembly using a suprapubic approach is illustrated in FIG. 6. The ends of the sling 11 are cut off and anchored in the abdominal region at the suprapubic incisions 400. FIG. 6 further shows tensioning suture 66. Tensioning suture 66 may be used to center and properly position the sling assembly 10 under the midurethra after the dilators 54 have been removed.

Figure 7:
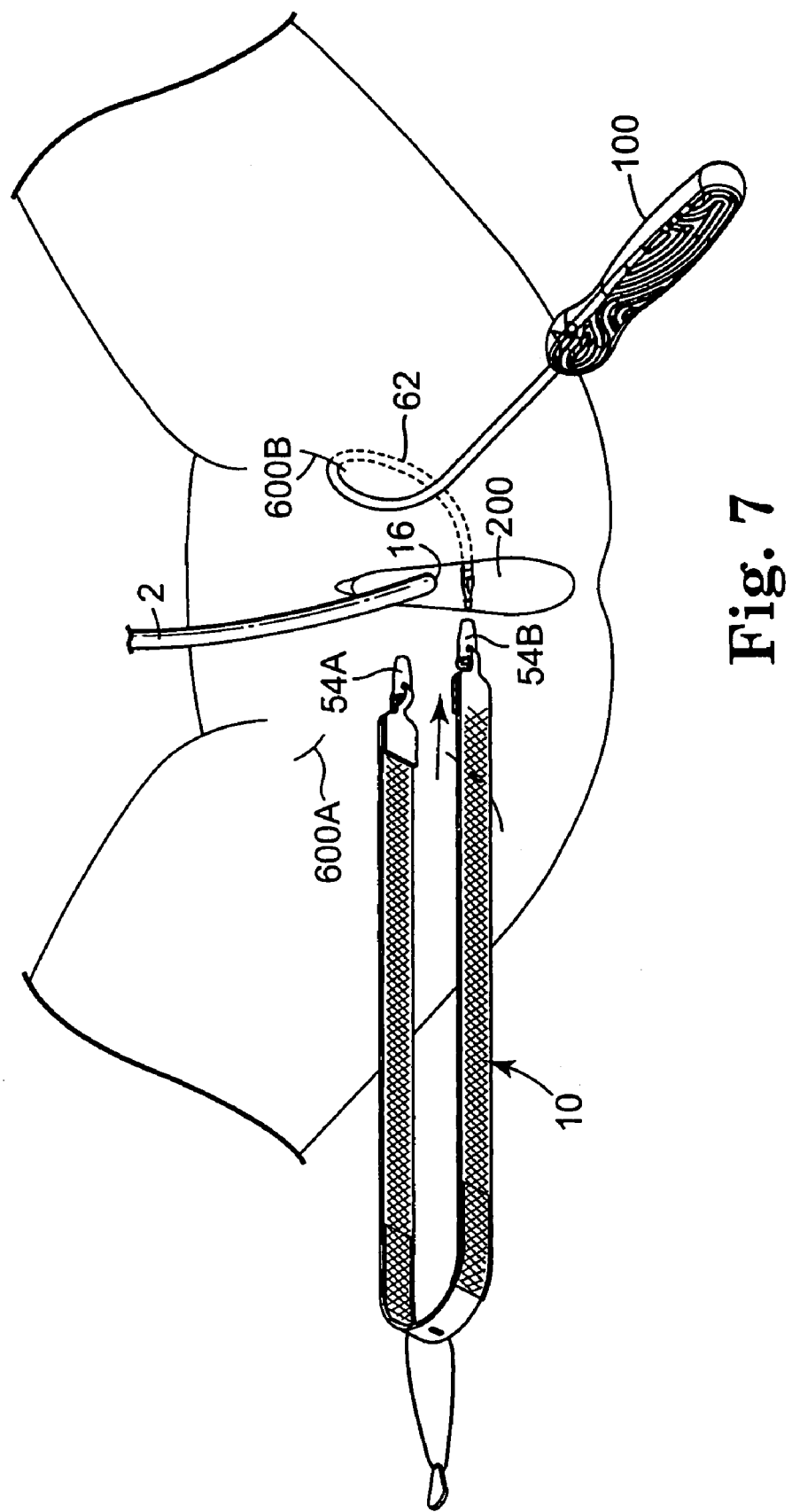
FIG. 7 illustrates the sheath assembly of the present invention in conjunction with a trans-obturator sling assembly.

FIG. 7 illustrates the sling assembly according to the present invention as it would be used in conjunction with a trans-obturator sling assembly. U.S. patent applications Ser. No. 10/306,179 filed Nov. 27, 2002 and No. 10/386,897 filed Mar. 11, 2003 describe a trans-obturator sling assembly and a method of use and are hereby incorporated herein by reference. The trans-obturator sling assembly includes a handle 100, a helical needle 62, and a sling assembly 10 according to the present invention. A Foley catheter 2 with a balloon is used to move the urethra 16 out of harms way in order to allow, among other things, a vaginal incision to be made. More precisely, a mediane paraurethral incision is made in the region of the middle third of the urethra. A finger is slipped in the vaginal incision and is guided to one side of the urethra in order to locate an obturator foramen. An incision 600B is made adjacent thereto in the groin region. Handle 100 is used to guide helical needle 62 through the incision 600B and out the vaginal incision. Dilator 54B is then attached to the needle 62 and the sling assembly is pulled through the vagina and out of the skin.

A finger is slipped in the vaginal incision and is guided to the opposite side of the urethra 16 in order to locate the second obturator foramen. An incision 600A is made adjacent thereto. A second helical needle shaped and sized to be used on the opposite side of the urethra is then passed through the skin incision 600A using handle 100 and out the vaginal incision. Dilator 54A is then attached to the second helical needle and the sling assembly is pulled through the vagina and out of the groin incision 600A. The sling assembly 10 is consequently positioned underneath the urethra. More particularly, the lower sheath 20 is positioned underneath the urethra 16.

Figure 8:
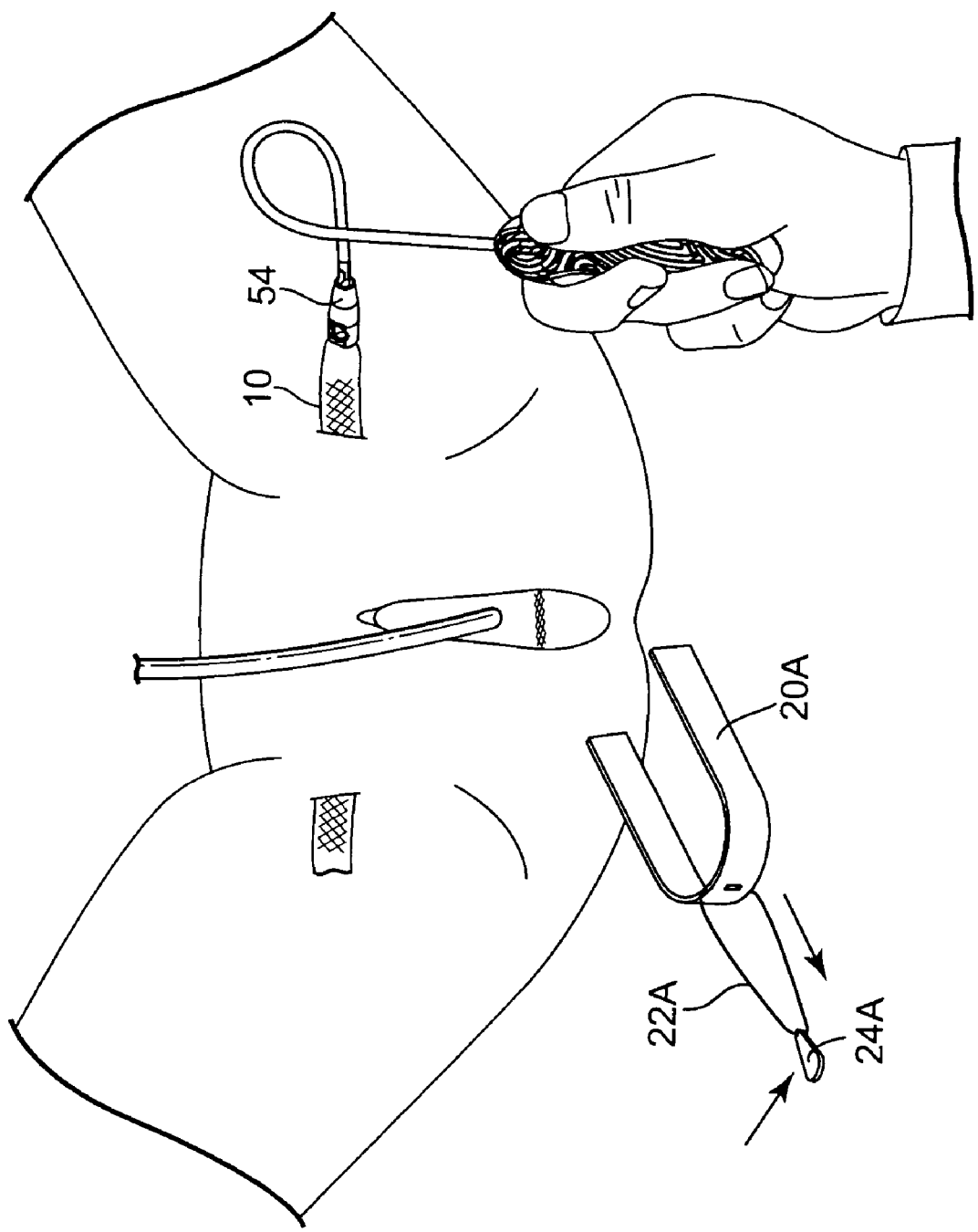
FIG. 8 illustrates the process of removing the lower sheath after the surgical sling has been positioned underneath the patient's urethra using the trans-obturator sling assembly system.

FIG. 8 illustrates the placement of the sling assembly 10 after the lower sheath 20A has been removed there from via the vaginal incision. As described above regarding the suprapubic approach, suture 22A is pulled by pulling tab 24A in order to remove the lower sheath 20A via the vaginal incision. FIG. 8 further illustrates that one of the dilators 54 has been cut-off. After the second dilator 54 is removed, as shown in FIG. 9, the upper sheaths 12A and 14A can be removed. As discussed above with regard to the suprapubic approach, a spacer (e.g., spacer 90) can be placed between the sling 11 and the urethra 16 after the lower sling 20A has been removed. As can be further seen from FIG. 9, the end of the sling 42 is anchored outside of the obturator foramen 3. FIG. 10 is a magnified view of the pubic region illustrated in FIG. 9.

Obviously, numerous modifications and variations of the present invention are possible in light of the above teachings. For example, the sheath assembly of the present invention can be used during a transvaginal approach. After a sling and the sheath assembly of the present invention is situated under the urethra, the lower sheath can be removed via the vaginal incision and the upper sheaths can be removed via the suprapubic incisions. It is therefore to be understood that within the scope of the appended claims, the invention may be practiced otherwise than as specifically described herein.

The invention claimed is:

1. A sling assembly, comprising:
  a surgical sling configured to be implanted during a surgical sling procedure, and including first and second regions and a central portion;
  a removable sheath assembly situated about the surgical sling, the removable sheath assembly comprising,
    first and second upper sheaths, the first upper sheath configured to be situated about the first region of the surgical sling, and the second upper sheath configured to be situated about the second region of the surgical sling, and
    a lower sheath, the lower sheath configured to be situated about the central portion of the surgical sling and to be in cooperative association with both the first and second upper sheaths,
    wherein said lower sheath defines an interior portion that envelopes the central portion of the surgical sling and an exterior portion which has first and second faces, the first face configured to be placed adjacent to a patient's urethra, and the first face includes a kiss cut.

2. The sling assembly of claim 1, further comprising a spacer configured to be placed between the surgical sling and the patient's urethra.

3. The sling assembly of claim 1, wherein the sling is elastic.

4. A sling assembly, comprising:
  a surgical sling configured to be implanted during a surgical sling procedure, and including first and second regions and a central portion;
  a removable sheath assembly situated about the surgical sling, the removable sheath assembly comprising,
    first and second upper sheaths, the first upper sheath configured to be situated about the first region of the surgical sling, and the second upper sheath configured to be situated about the second region of the surgical sling, and
    a lower sheath, the lower sheath configured to be situated about the central portion of the surgical sling and to be in cooperative association with both the first and second upper sheaths,
  wherein the lower sheath defines an interior portion that envelopes the surgical sling and an exterior portion which has first and second faces, the first face configured to be placed adjacent to a patient's urethra, and the second face has a tab portion operatively associated therewith to assist in removal of the lower sheath from the sling.

5. A sling assembly, comprising:
  a surgical sling configured to be implanted during a surgical sling procedure, and including first and second regions and a central portion;
  a removable sheath assembly situated about the surgical sling, the removable sheath assembly comprising,
    first and second upper sheaths, the first upper sheath configured to be situated about the first region of the surgical sling, and the second upper sheath configured to be situated about the second region of the surgical sling, and
    a lower sheath, the lower sheath configured to be situated about the central portion of the surgical sling and to be in cooperative association with both the first and second upper sheaths,
  wherein the lower sheath defines an interior portion that envelopes the surgical sling and an exterior portion which has first and second faces, the first face configured to be placed adjacent to a patient's urethra, and the sling assembly further comprises a removal assembly operatively associated with the lower sheath to assist in separating the lower sheath from the sling.

6. The sling assembly of claim 5, wherein the removal assembly includes a tube situated within the lower sheath and a suture which operatively associates the tube and a tab portion.

7. A sling assembly, comprising:
  a surgical sling configured to be implanted during a surgical sling procedure, and including first and second regions and a central portion;
  a removable sheath assembly situated about the surgical sling, the removable sheath assembly comprising,
    first and second upper sheaths, the first upper sheath configured to be situated about the first region of the surgical sling, and the second upper sheath configured to be situated about the second region of the surgical sling, and
    a lower sheath, the lower sheath configured to be situated about the central portion of the surgical sling and to be in cooperative association with both the first and second upper sheaths,
  further comprising a dilator for creating or expanding a tissue passageway for placement of said sling.

8. A method for implanting a sling to treat urinary incontinence in a patient comprising the steps of:
  providing a sling assembly including,
    a surgical sling including first and second regions and a central portion, and
    a removable sheath assembly including first and second upper sheaths and a
  lower sheath;

creating at least one vaginal incision;

creating at least one suprapubic incision;

positioning the sling assembly such that the central portion of the surgical sling and the lower sheath are placed underneath the patient's urethra;

removing the lower sheath via the at least one vaginal incision; and removing the first and second upper sheaths via the at least one suprapubic incision.

9. The method of claim 8, wherein the lower sheath includes a removal assembly and the step of removing the lower sheath includes the step of:

pulling the removal assembly in order to remove the lower sheath from the sling.

10. The method of claim 8, further comprising the step of: placing a spacer between the sling and the patient's urethra after the step of removing the lower sheath.

11. The method of claim 8, wherein the step of removing the lower sheath occurs prior to the step of removing the first and second upper sheaths.

12. The method of claim 8, wherein the step of removing the first and second upper sheaths occurs prior to the step of removing the lower sheath.

13. The method of claim 8, further comprising the step of:

placing a spacer between the sling and the patient's urethra prior to either removing step.

14. The method of claim 13, further comprising the step of:

removing the spacer from between the sling and the patient's urethra;

wherein the step of removing the first and second upper sheaths occurs prior to the step of removing the spacer and the step of removing the spacer occurs prior to removing the lower sheath.

15. A method for implanting a sling to treat urinary incontinence in a patient comprising the steps of:

providing a sling assembly including, a surgical sling including first and second regions and a central portion, a removable sheath assembly including first and second upper sheaths and a lower sheath, and a spacer;

creating at least one vaginal incision;

creating at least one suprapubic incision;

positioning the sling assembly such that the central portion of the surgical sling and the lower sheath are placed underneath the patient's urethra;

removing the lower sheath via the at least one vaginal incision;

removing the first and second upper sheaths via the at least one suprapubic incision; and removing the spacer.

* * * * *